United States Patent

Buchwald et al.

[11] Patent Number: 5,888,688
[45] Date of Patent: Mar. 30, 1999

[54] DIFLUOROMETHOXY-2, 2, 2-TRIFLUOROETHANE COMPOSITIONS AND METHODS OF USE

[75] Inventors: Hans Buchwald, Ronnenberg; Joachim Hellmann, Hanover; Boleslaus Raszkowski, Wiedensahl, all of Germany

[73] Assignee: Solvay Fluor und Derivate GmbH, Hanover, Germany

[21] Appl. No.: 848,650

[22] Filed: Apr. 29, 1997

Related U.S. Application Data

[62] Division of Ser. No. 498,770, Jul. 6, 1995, Pat. No. 5,674,825.

[30] Foreign Application Priority Data

Jul. 15, 1994 [DE] Germany ............................. 4425066.5

[51] Int. Cl.[6] .................................................. G03G 13/20
[52] U.S. Cl. ............................ 430/124; 430/97; 427/335
[58] Field of Search ...................... 430/97, 124; 427/335; 510/411, 412, 415, 175, 177, 178; 252/67, 69

[56] References Cited

U.S. PATENT DOCUMENTS

| | | |
|---|---|---|
| 3,761,524 | 9/1973 | Terrell et al. . |
| 3,846,332 | 11/1974 | Croix . |
| 3,950,168 | 4/1976 | Erhardt et al. ........................... 430/124 |
| 4,311,723 | 1/1982 | Mugrauer ............................... 427/14.1 |
| 5,120,462 | 6/1992 | Buchwald ............................... 510/411 |
| 5,304,320 | 4/1994 | Barthelemy et al. ..................... 252/67 |
| 5,399,281 | 3/1995 | Buchwald et al. ....................... 510/175 |
| 5,413,730 | 5/1995 | Barthelemy et al. ..................... 134/12 |
| 5,529,618 | 6/1996 | Buchwald et al. ..................... 106/38.22 |

FOREIGN PATENT DOCUMENTS

| | | |
|---|---|---|
| 450458 | 3/1991 | European Pat. Off. . |
| 465037 | 1/1992 | European Pat. Off. . |
| 528481 | 2/1993 | European Pat. Off. . |
| 2029325 | 3/1980 | United Kingdom . |
| WO 93/10485 | 5/1993 | WIPO . |

OTHER PUBLICATIONS

Chemical Abstracts, vol. 97, No. 12 (Sep. 20, 1982), Columbus, Ohio abstract No. 101693m.

*Primary Examiner*—Janis L. Dote
*Attorney, Agent, or Firm*—Evenson, McKeown, Edwards & Lenahan, P.L.L.C.

[57] ABSTRACT

The present invention relates to new uses of difluoromethoxy-2,2,2-trifluoroethane (E245) or of compositions which contain difluoromethoxy-2,2,2-trifluoroethane together with a further solvent (cosolvent). The invention furthermore relates to new compositions of E245 as a mixture with some of these solvents. A preferred process of use is fixing toner applied to a recording material in the fixing device of a printing or copying apparatus by means of a fixing vapor composed of difluoromethoxy-2,2,2-trifluoroethane (E245) alone or in admixture with a cosolvent.

11 Claims, 1 Drawing Sheet

DIFLUOROMETHOXY-2, 2, 2-TRIFLUOROETHANE COMPOSITIONS AND METHODS OF USE

This application is a division of application Ser. No. 08/498,770, filed Jul. 6, 1995, now issued U.S. Pat. No. 5,674,825.

BACKGROUND OF THE INVENTION

The present invention relates to new uses of difluoromethoxy-2,2,2-trifluoroethane (E245) and of compositions which comprise a further solvent (cosolvent) in addition to difluoromethoxy-2,2,2-trifluoroethane. The invention furthermore relates to new compositions of E245 as a mixture with some of these solvents. A preferred use is a process for fixing toner applied to a recording material in the fixing device of a printer and/or copier by means of fixing vapor composed of E245. In this process, E245 may be used as such or as a mixture with a cosolvent.

In the printing and copying operation, a charge image (negative image) is produced initially on a photoconductor drum by exposure of the print or copy master to light and is developed in a subsequent developer station, i.e. the charge image is provided with toner. The developed charge images on the photoconductor drum then pass to a transfer station. An electrostatic field which exists in the transfer station draws the toner image over onto a record carrier, for example a web of paper or else an individual sheet, fed to the transfer station. The toner image now adheres to the surface of the record carrier, although it can be wiped off. The record carrier provided with the toner image (positive image) is then passed through a fixing device. A solvent vapor required for fixing the toner is generated in this fixing device. For this purpose, the solvent is located at the base of the housing of the fixing device. The base of the fixing device is heated by means of a heating device, so that the solvent vaporizes from the base. The resulting solvent vapor acts on the record carrier, and in particular on the toner applied thereto. In this process, so-called cold fixing, the solvent vapor thus ensures intimate contact between the toner and the recording material. The toner is thereby partially dissolved, so that it can penetrate into the record carrier. After this fixing operation, the record carriers are freed from any still adhering residues of the solvent vapor by drying, and a dry, firmly adhering toner image, which cannot be wiped off, is obtained on the record carrier.

Solvents for fixing the toner must meet particular requirements. Such solvents should have a relatively low boiling point and be non-flammable and essentially non-toxic, and should have favorable dissolving properties for, for example, toner particles which are applied to a recording material and are to be fixed by partial dissolving. As a rule, these requirements cannot be met by only a single solvent. A large number of solvent mixtures with more or less different compositions are therefore used in practice. It is therefore known in the prior art (for example in the field of industrial cleaning processes or in vapor degreasing), in addition to using pure chlorinated and/or fluorinated hydrocarbons, also to employ mixtures of chlorofluorohydrocarbons (as the primary solvent) with a cosolvent. Such mixtures can be either non-azeotropic or azeotropic or azeotrope-like. As used herein, the term "azeotrope-like" refers to mixtures which have an essentially constant boiling point (change in the boiling point by not more than 5° C.) over a relatively wide mixing and concentration range. Such azeotrope-like mixtures therefore behave like azeotropes when used in practice. Those solvent mixtures which have a constant boiling point (maximum variation ±0.5° C.) and which, on boiling, contain the solvent components of the mixture in the same relative composition in the vapor phase as in the liquid phase are referred to as azeotropes. Solvent mixtures which are suitable for use in fixing devices of printing and copying apparatus as a rule comprise at least two solvent components, at least one component of which must have the property of partially dissolving the toner. Since in modern fixing devices these solvent mixtures act on the toner in the vapor state, the most uniform possible vaporization of solvent mixtures, which are suitable in practice, is required, i.e. vaporization properties without separation into the components or at least without relatively large shifts in the ratios of the amounts of the components in the vapor phase relative to the liquid phase. The solvent mixture employed in the fixing device thus advantageously has at least azeotrope-like, but in particular azeotropic, boiling properties so that a constantly good fixing of the toner on the recording material can also be assured over relatively long periods of use.

The use of solvents in the fixing device of printing or copying apparatuses has already been described. For example, German Patent Application No. DE 2,835,284 -discloses azeotropic mixtures of trichlorotrifluoroethane (R113) and acetone. This specification also contains further details on the process of fixing the toner in a printing or copying operation.

Another process using partly halogenated chlorofluorohydrocarbons is described in WO 93/10485. In this process 2,2-dichloro-1,1,1-trifluoroethane (R123) and 1,1-dichloro-1-fluoroethane (R141b) are proposed as the primary solvent. Disadvantages include, however, that on the one hand the R123 proposed is not completely acceptable toxicologically under certain circumstances, and on the other hand R141b may be incompatible with other materials which may limit its use.

Although some efforts have already been made in the prior art to discover alternative compositions having the desired properties for various fields of use as substitutes for the completely halogenated hydrocarbons used heretofore, there remains a need for improvement on the basis of the use properties, toxicological properties and properties which affect the environment. For example, known solvent mixtures comprise relatively large amounts of solvents which in some cases are unacceptable toxicologically or environmentally or from a safety point of view (low flash point). For a number of solvent constituents, substitution by other solvents which are at least equally suitable for the particular intended uses is desirable because of their properties which affect the environment.

SUMMARY OF THE INVENTION

It is therefore the object of the invention to provide solvents and solvent mixtures which are especially suitable in particular for use as toner solvents in the fixing device of printing and/or copying apparatus.

This and other objects of the invention are achieved by providing a method of using difluoromethoxy-2,2,2-trifluoroethane as a solvent for fixing toner particles applied to a recording material, for example in the fixing device of a printing and/or copying apparatus, especially a laser printer. Difluoromethoxy-2,2,2-trifluoroethane, which is generally also referred to as E245, is already known and can be prepared, for example, by reacting trifluoroethanol with chlorodifluoromethane, as described, for example, in U.S.

Pat. No. 3,761,524. It has been found according to the invention that E245 has favorable solvent properties for use in the above-mentioned method as well as the further uses also described below. E245 shows favorable swelling properties on various plastics and also on elastomers. Polar organic compounds are readily soluble in E245. E245 furthermore is also suitable for uses where it is desirable to add non-polar additives; in which case, the solubility of the non-polar additives can be improved by use of suitable solubilizing agents. Furthermore, E245 is readily compatible with many plastics which are attacked by the completely and partly halogenated chlorofluorohydrocarbons used heretofore in the prior art. Furthermore, E245 is non-combustible and has no flash point. The boiling point of E245 under atmospheric pressure is 29° C.

The difluoromethoxy-2,2,2-trifluoroethane used according to the invention is therefore already suitable as such for fixing, in particular for fixing polar toner particles; however, usable fixing results can also be achieved with non-polar toner particles using difluoromethoxy-2,2,2-trifluoroethane as the solvent. The fixing properties can be improved over the sole use of E245 by addition of cosolvents and optionally also by addition of solubilizing agents (for example when non-polar additives are used). In a preferred embodiment of the invention, E245 is therefore used as the primary solvent in combination with a cosolvent. Such cosolvents may include, in particular, the cosolvents contained in customary fixing solvents.

E245 is also particularly suitable as a mixture with cosolvents for further uses, for example cleaning uses. Cosolvents for use as a fixing agent are advantageously selected from the group consisting of lower alcohols, ketones, esters and, where appropriate, the chlorinated hydrocarbons (CHCs). In addition to the aforementioned cosolvents, glycols are also suitable for cleaning uses.

Examples of lower alcohols which are suitable as cosolvents include, in particular, C1- to C3-alcohols, for example methanol, ethanol, propanol and isopropanol. Examples of suitable ketones include, in particular, the C3-to C6-ketones; for example acetone, methyl ethyl ketone and methyl isobutyl ketone. Acetone is the preferred ketone. Examples of suitable esters include, in particular, the esters of C2- to C3-carboxylic acids with lower alcohols (C1- to C3-alcohols). For example, esters of acetic acid or propionic acid with the C1- to C2-alcohols methanol or ethanol are advantageous. Preferred esters include, for example, methyl acetate and ethyl acetate, but also methyl propionate. The other group of cosolvents, i.e. the chlorinated hydrocarbons, are low molecular weight hydrocarbons, i.e. C1- to C2-hydrocarbons, which are substituted by one or more chlorine atoms. Optionally, the chlorinated hydrocarbons can also additionally carry fluorine atoms. Preferred chlorinated hydrocarbons (CHCs) for use as cosolvents for E245 according to the invention include methylene chloride and trichloroethylene. Examples of suitable glycols (only for cleaning uses) includes, in addition to the parent compound (ethylene glycol), the generic diols in which the hydroxyl groups are in the vicinal arrangement (1,2-diols), and also those compounds with non-adjacent OH groups as well as those compounds in which one of the two OH groups is etherified by a C1- to C4-alkyl radical. The glycols employed according to the invention may contain from 2 to 10 carbon atoms. Examples of glycols which can be used according to the invention include ethylene glycol, propylene glycols and butylene glycols, and in particular butylglycol (2-butoxy-ethanol).

For the use according to the invention of binary compositions of E245 as the primary solvent and of lower alcohols, ketones, esters and/or CHCs as cosolvents for fixing toner particles, those binary compositions which have at least azeotrope-like, but in particular azeotropic, properties are preferred. In general, the cosolvent is then present in an amount of 0.2 to 5.0% by weight, in particular 0.3 to 5.0% by weight, and the primary solvent E245 accordingly in an amount of 99.8 to 95.0% by weight or 99.7 to 95.0% by weight. In azeotropic binary compositions, the amount of cosolvent is between 0.3 and 3.0% by weight, depending on the nature of the cosolvent, and the amount of E245 is accordingly 99.7 to 97.0% by weight. In each of these cases, the constituent percentages should add up to 100% by weight. Such azeotrope-like and azeotropic compositions can be determined by distillation experiments with a mixture of the primary solvent and cosolvent and subsequent analysis of the particular composition of the vapor and liquid phases.

Binary azeotrope-like compositions of E245 and lower alcohols are already described in European Patent Application EP 600,538 for cleaning electronic components and for degreasing metal components, and reference may be made to the content of EP 600,538 for the preparation of azeotrope-like and azeotropic compositions of E245 and lower alcohols and for the quantity ranges of the two components disclosed for this purpose. For example, one azeotropic composition mentioned therein comprises about 97% by weight of E245 and about 3% by weight of methanol; the boiling point under atmospheric pressure (1 bar) is about 29.3° C. Another azeotropic composition comprises 99.7% by weight of E245 and 0.3% by weight of ethanol; the boiling point is 74.9° C. under 4 bar.

In contrast, the binary compositions of E245 and the cosolvents selected from the group consisting of ketones, esters and chlorinated hydrocarbons used according to the invention for fixing toners have not been described heretofore in the prior art. Applicants have found that in addition to their suitability for use in fixing toners, compositions of E245 with the above cosolvents are also suitable for solvent and cleaning uses. It has furthermore also been found that compositions of E245 with a cosolvent selected from the group consisting of glycols are particularly suitable for cleaning uses.

The invention therefore also relates to the new compositions of difluoromethoxy-2,2,2-trifluoroethane and a cosolvent selected from the group consisting of ketones, esters, chlorinated hydrocarbons and glycols. Advantageous compositions are characterized by a content of 99.8 to 50.0% by weight of difluoromethoxy-2,2,2-trifluoroethane and 0.2 to 50.0% by weight of cosolvent selected from the group consisting of ketones, esters, chlorinated hydrocarbons and glycols. Preferred compositions for cleaning uses comprise 99.8 to 90.0% by weight of difluoromethoxy-2,2,2-trifluoroethane and 0.2 to 10.0% by weight of a cosolvent selected from the group consisting of ketones, esters, chlorinated hydrocarbons and glycols. Compositions containing E245 with cosolvents selected from the group consisting of ketones, esters and CHCs, in some cases also show usable results in fixing toner particles. Compositions which comprise the cosolvent selected from the group consisting of ketones, esters and CHCs in an amount of 0.2 to 5.0% by weight, in particular 0.3 to 5.0% by weight, and the primary solvent E245 accordingly in an amount of 99.8 to 95.0% by weight or 99.7 to 95.0% by weight are advantageous in this case. Preferably, the cosolvent selected from the group consisting of ketones, esters and CHCs is present in an amount of 0.3 to 5.0% by weight; the amount of E245 is then 99.7 to 5.0% by weight. In each case the sum of the constituent percentages of the above compositions should add up to 100% by weight.

Compositions according to the invention of difluoromethoxy-2,2,2-trifluoroethane and a glycol, preferably butylglycol, are particularly preferred for cleaning uses.

Preferred compositions which are outstandingly suitable for the use according to the invention for fixing toner particles comprise, in addition to the primary solvent difluoromethoxy-2,2,2-trifluoroethane, a cosolvent selected from the group consisting of ketones, preferably acetone.

In a particularly advantageous variant of the invention, the compositions of difluoromethoxy-2,2,2-trifluoroethane and acetone are distinguished by azeotrope-like or in particular azeotropic properties. Such azeotrope-like or azeotropic compositions of solvents have a number of advantages in use. On the one hand, they have a constant or essentially constant boiling point (variations in the boiling point by not more than about ±0.5° C.), and on the other hand the composition of the mixtures thereby also remains constant or essentially constant. Thus, when azeotropic or azeotrope-like compositions are used, fractionation of the solvent constituents of the compositions does not occur, which means that undesirable changes in properties, such as, for example, a changed dissolving power, reduced inertness towards objects to be cleaned or increased flammability if ignitable cosolvents are used, are avoided. Furthermore, azeotropic or azeotrope-like compositions can easily be purified by conventional distillation after use and are therefore available in a simple manner for re-use, without the characteristics of the original composition being lost.

It has now been found that some compositions of E245 and acetone according to the invention have very narrow boiling ranges and therefore have at least azeotrope-like properties. These special azeotrope-like compositions comprise 99.5 to 95.0% by weight of difluoromethoxy-2,2,2-trifluoroethane (E245) as a mixture with 0.5 to 5.0% by weight of acetone, these compositions boil in a range from about 28.5 to about 33.0° C. (atmospheric pressure=1 bar). The azeotropic composition consisting of about 97.2% by weight of difluoromethoxy-2,2,2-trifluoroethane and about 2.8% by weight of acetone, which has a boiling point of about 28.5° C. under atmospheric pressure, is particularly advantageous.

The azeotropic and azeotrope-like compositions of difluoromethoxy-2,2,2-trifluoroethane and acetone according to the invention have advantageous dissolving properties. As a result, in addition to being suitable as solvents in fixing devices of printing and copying apparatus, they are also suitable for other intended uses, for example as solvents.

The compositions of E245 and acetone according to the invention are clear solutions at room temperature, to which known additives can be added (the relative ratio of difluoromethoxy-2,2,2-trifluoroethane to acetone specified by the above % by weight data is not thereby changed). Likewise, known additives can also be added to the other compositions according to the invention of E245 and a cosolvent selected from the group consisting of ketones, esters, CHCs and glycols as well as to the compositions of E245 and lower alcohols (the relative ratio of E245 to the cosolvent likewise being retained). The additives are described together hereinafter for all the compositions.

Stabilizers are one group of known additives. This group comprises those compounds which prevent an undesirable reaction of constituents of the composition with one another or with other reaction partners, such as, for example, atmospheric oxygen, metal, water and the like. Known stabilizers include, for example, nitroalkanes, particularly nitromethane and nitroethane, alkylene oxides, particularly butylene oxide, or branched alkynols, such as, for example, 2-methyl-but-3-yn-2-ol. These stabilizers can be used individually or in combination with one another. Stabilizer amounts of from 0.01 to 5% by weight, preferably 0.05 to 1% by weight, based on the total mixture weight, are especially suitable.

Another group of known additives comprises compounds selected from the group consisting of corrosion inhibitors, nonionic or ionic emulsifiers, dyestuffs and the like.

The compositions according to the invention also have possible uses in the fields of cleaning and/or vapor degreasing, especially when glycols are used as cosolvents. In these generally known processes, the object to be cleaned is dipped in liquid and/or vaporous cleaning mixture or sprayed with liquid cleaning mixture in one or more stages. The cleaning action in such processes can be increased by use at the boiling point and/or by application of ultrasound and/or by agitation. Improvement in the cleaning action by a mechanical action, such as, for example, brushing, is also known.

For example, the electronic industry predominantly uses organic resin fluxes for soldering processes, and the excess flux must be removed from printed circuit boards after the soldering operation. This is done with organic solvents which are compatible with the printed circuit boards and the electronic components, i.e. the solvent must not react with the board or any of the components. The resin fluxes to be removed are mixtures of polar and non-polar compounds and often additionally comprise special activators. Difluoromethoxy-2,2,2-trifluoroethane by itself is not effective for removal of the polar components of the resins. It is also not capable by itself of completely removing special fluxes, particularly fluxes containing high amounts of activator. Surprisingly, however, the compositions according to the invention of E245 and glycols, for example butylglycol, can remove both the polar and the non-polar components and are therefore effective on a broad basis as removal agents for resin fluxes, in particular those containing high amounts of activator.

Unassembled and assembled printed circuit boards (including in particular those with SMDs) can thus also be cleaned without problems using the compositions according to the invention of E245 and butylglycol (2-butoxy-ethanol) if fluxes having a high activator content are used, without the feared "white deposits" which occur when conventional cleaning agents are used.

The new azeotrope-like and azeotropic compositions according to the invention (with the exception of the compositions with glycols as the cosolvent), and especially the compositions with acetone as a cosolvent, are particularly advantageous systems for fixing toners to record carriers in printing and copying apparatus. The compositions according to the invention used for this purpose may also comprise stabilizers. The compositions according to the invention, especially the azeotrope-like or azeotropic compositions of E245 and acetone, very readily partially dissolve, in particular, dry toners composed of polystyrene. Such toners can have, for example, an un-crosslinked polymer matrix. For example, such toners can have a polymer matrix of polystyrene and methacrylates. The compositions according to the invention, especially compositions of E245 and acetone, are outstandingly suitable for use for fixing toners, in particular in modern laser printers. They are also suitable if the record carrier has a high degree of coloration, and in particular are also readily compatible with all the customary grades of paper. Problems of underfixing such as are often observed with prior art fixing solvents are not to be feared. Furthermore, the compositions according to the invention, in particular the azeotrope-like and azeotropic compositions of E245 and acetone—as well as the compositions of E245 and C1- to C3-alcohols or of E245 and CHCs used according to the invention—have very good partial dissolving properties for toners, in particular for dry toners based on polystyrene. The compositions according to the invention or which are used according to the invention are capable of very readily partially dissolving the toner particles on the one hand, without on the other hand leading to an undesirable running of the toner on the record carrier. It is thereby possible to produce firmly adhering images on the record carrier which cannot be wiped off and which have a high resolution and sharpness.

The compositions of E245 according to the invention which comprise special cosolvents, for example glycols, assure to a great extent the high degree of purity which is required in special fields of use, for example for cleaning components and printed circuit boards in the electronics industry. They are not inferior in their properties to the previously known compositions in the prior art which contain fully halogenated chlorofluorohydrocarbons.

Another advantage of the compositions according to the invention is their advantageous flash point characteristics, which can be tested, for example, via the "closed crucible" method. New solutions to problems in many fields of use are therefore made possible by the compositions according to the invention. It is also advantageous that the solvent employed, i.e. difluoromethoxy-2,2,2-trifluoroethane, decomposes significantly more readily than do completely halogenated chlorofluorohydrocarbons and has a low global warming potential, and thus is significantly more environmentally acceptable.

BRIEF DESCRIPTION OF THE DRAWINGS

The invention will be illustrated in further detail hereinafter by the following use examples without, however, being limited in its scope thereby. Unless otherwise stated, percentages are expressed as % by weight.

EXAMPLE 1

Figure 1:
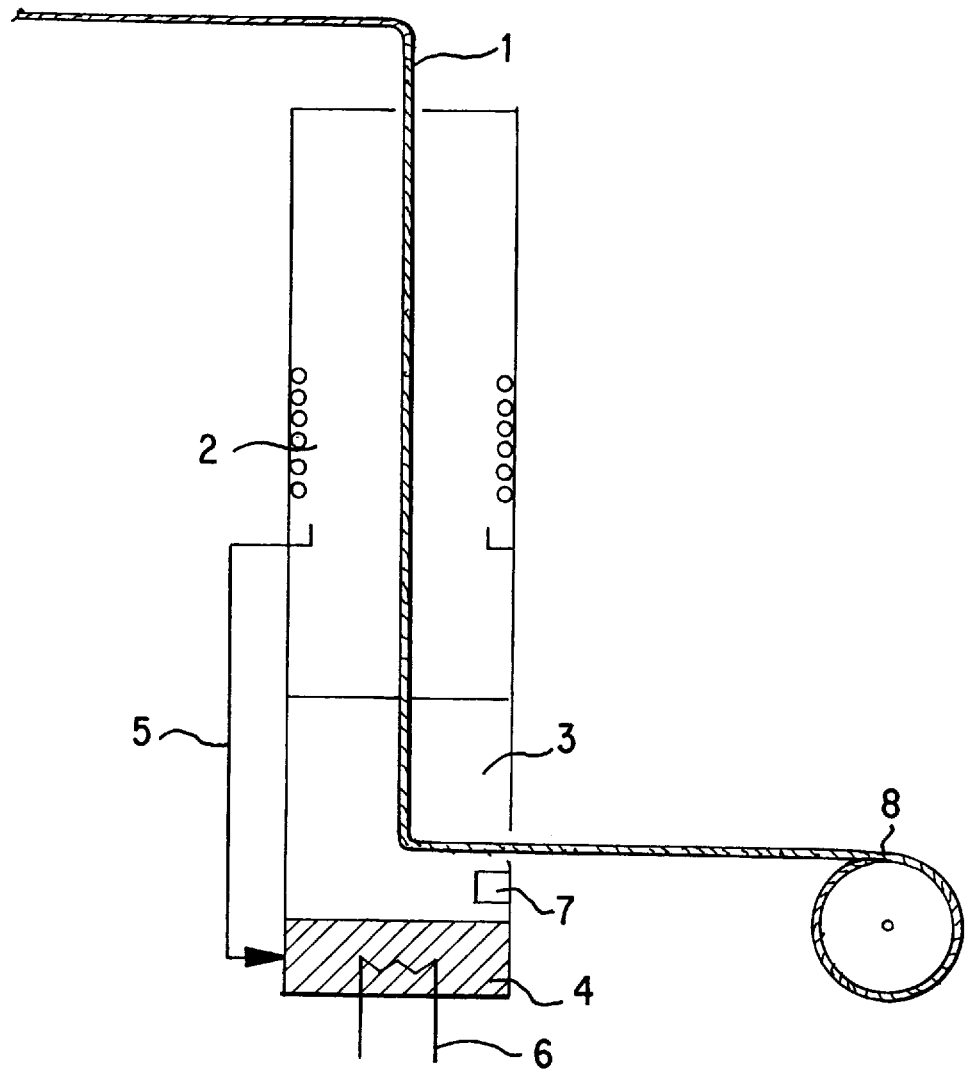
FIG. 1 is a drawing of a cold fixing station in which 1 represents a web of paper charged with toner; 2 represents a cold trap; 3 represents a vapor chamber; 4 represents a solvent vaporization device; 5 represents a solvent return; 6 represents a heating device; 7 represents an ultrasound vapor sensor for measuring vapor concentration, and 8 represents a winder unit.

Toner fixing.

The compositions proposed according to the invention for use as solvents for fixing toner particles can be tested for their suitability in principle for fixing using a cold fixing station having the basic features shown schematically in FIG. 1. For this purpose, a web of paper is charged with a polystyrene-based toner, for example in the form a pattern or a sequence of numbers or letters (for example sequence of symbols of a particular type of script). This charging can be done in a known manner, for example in which charge images formed by the electrostatic principle are initially developed in a developer station with the aid of toner powder to give "toner images," and these toner images are then transferred to a record carrier (for example web of paper) in a transfer station. These toner images adhere loosely to the record carrier and must then be "fused into" the record carrier by partial dissolution in order to assure smudge-free fixing. The fusing of the toner into the web of paper (=record carrier) occurs with the aid of the solvent vapor (E245 or a mixture of E245 with one of the cosolvents described for this purpose in an azeotrope-like or azeotropic composition). For this purpose, a solvent vapor is generated which is capable of partially dissolving the toner on the record carrier, so that the toner can then penetrate into the record carrier to a sufficient extent. For this purpose, the recording material provided with the toner image is introduced into a fixing device, for example according to FIG. 1, in which the solvent vapor can then act on the recording material. Such a fixing device comprises, for example, a housing with a feed device for the record carrier which serves to pass the record carrier through the housing. The fixing device further comprises a vaporization station in which the solvent vapors can be held as far as possible without escaping. The entry and exit points of the fixing device are therefore provided with cold traps and seals. The vaporization and fixing agent concentration are regulated by conventional control mechanisms.

The solvent vapors composed of E245 used according to the invention show good partial dissolving properties for toners. The toner can in each case be readily "fused into" (fixed in) the recording material without the edges running. Images which are well fixed (smudge-free) and have a good sharpness can be produced on the recording materials.

EXAMPLE 2

Cleaning of Printed Circuit Boards.

Cleaning experiments with printed circuit boards which were contaminated both with conventional halogen-containing solder fluxes and with solder fluxes having high activator contents were carried out in a commercially available three-chamber cleaning unit. Both the contamination by conventional halogen-containing solder fluxes and that by solder fluxes with high activator contents could be removed from the printed circuit boards with outstanding cleaning results. The cleaning compositions, cleaning conditions and cleaning results are shown in Table 1.

TABLE 1

| No. | Compositions for bath 1 | Cleaning conditions | Result |
|---|---|---|---|
| 1 | E245/butylglycol: 90.0%/10.0% | 3-bath: 1) 3 minutes ultrasound 2) 1 minute ultrasound 3) 1 minute vapor degreasing (in bath 2 and 3: E245) | ++ |
| 2 | E245/butylglycol: 95.0%/5.0% | 3-bath: 1) 3 minutes ultrasound 2) minute ultrasound 3) 1 minute vapor degreasing (in bath 2 and 3: E245) | ++ |

In the cases identified by "++" in the "result" column, a very good cleaning action was achieved and there was no formation of "white deposits". It can easily be seen that the compositions according to the invention have outstanding cleaning capacities.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of fixing a toner in a fixing device of a printer or copier, comprising:

contacting a toner image on a record carrier with a fixing vapor comprising difluoromethoxy-2,2,2-trifluoroethane and a cosolvent selected from the group consisting of C1 to C3 alcohols, ketones, and esters.

2. A method according to claim 1, wherein said fixing device is a fixing device for a laser printer.

3. A method according to claim 1, wherein said toner is a polystyrene-based toner.

4. A method according to claim 1, wherein said fixing vapor is vapor of an azeotrope-like mixture of difluoromethoxy-2,2,2-trifluoroethane and said cosolvent, said mixture having a boiling point in the range from about 28.5 to about 33.0° C. at 1 bar.

5. A method according to claim 1, wherein said cosolvent is a ketone.

6. A method according to claim 5, wherein said cosolvent is acetone.

7. A method according to claim 1, wherein said fixing vapor consists essentially of from 0.2 to 5.0% by weight of said cosolvent and from 99.8 to 95.0% by weight of difluoromethoxy-2,2,2-trifluoroethane for a total of 100%.

8. A method according to claim 7, wherein said fixing vapor consists essentially of from 0.3 to 5.0% by weight of said cosolvent and from 99.7 to 95.0% by weight of difluoromethoxy-2,2,2-trifluoroethane, for a total of 100%.

9. A method according to claim 8, wherein said fixing vapor is an azeotropic binary composition consisting essentially of 97.2% by weight of difluoromethoxy-2,2,2-trifluoroethane and 2.8% by weight of said cosolvent, wherein said cosolvent is acetone.

10. A process for fixing a polystyrene toner which has been applied to a record carrier, said process comprising:

vaporizing a solvent in a fixing device of a printing or copying apparatus, said solvent comprising an azeotrope-like or azeotropic mixture which has partial dissolving properties for the toner, and allowing the vaporized solvent to act on the toner and partially dissolve the toner, wherein the mixture comprises difluoromethoxy-2,2,2-trifluoroethane and a cosolvent selected from the group consisting of C1–C3 alcohols, ketones, and esters.

11. A process according to claim 10, wherein said solvent further comprises a stabilizer.

* * * * *